(12) United States Patent
Gehrke et al.

(10) Patent No.: US 6,670,557 B2
(45) Date of Patent: Dec. 30, 2003

(54) DESIGN FOR CONSTRUCTING AN INPUT CIRCUIT TO RECEIVE AND PROCESS AN ELECTRICAL SIGNAL

(75) Inventors: Martin Gehrke, Weinstadt (DE); Torsten Pechstein, Waldheim (DE)

(73) Assignee: Endress & Hauser Conducta Gesellschaft fur Mess-und Regeltechnik mbH & Co., Gerlingen (DE)

( * ) Notice: Subject to any disclaimer, the term of this patent is extended or adjusted under 35 U.S.C. 154(b) by 0 days.

(21) Appl. No.: 10/001,668

(22) Filed: Oct. 23, 2001

(65) Prior Publication Data

US 2002/0139573 A1 Oct. 3, 2002

(30) Foreign Application Priority Data

Oct. 23, 2000 (DE) .......................................... 100 52 532

(51) Int. Cl.⁷ ................................................. H05K 1/16
(52) U.S. Cl. ........................ 174/260; 174/255; 174/256; 174/52.2; 361/760; 361/737; 361/800; 257/788
(58) Field of Search ................................ 174/256, 255, 174/260, 261, 52.2, 52.3, 52.4; 361/760, 792, 737, 795, 800, 818; 257/778, 788, 711

(56) References Cited

U.S. PATENT DOCUMENTS

| | | | |
|---|---|---|---|
| 4,513,355 A | * 4/1985 | Schroeder et al. ........... 361/767 |
| 5,173,844 A | * 12/1992 | Adachi et al. ............... 361/792 |
| 5,521,332 A | * 5/1996 | Shikata et al. .............. 174/52.4 |
| 5,646,828 A | * 7/1997 | Degani et al. ............... 361/715 |
| 5,689,091 A | * 11/1997 | Hamzehdoost et al. ...... 174/255 |
| 5,847,935 A | * 12/1998 | Thaler et al. ................ 361/761 |
| 5,939,214 A | * 8/1999 | Mahulikar et al. .......... 428/626 |
| 6,014,318 A | * 1/2000 | Takeda ........................ 361/764 |
| 6,088,901 A | * 7/2000 | Huber et al. ................ 29/469.5 |
| 6,160,311 A | * 12/2000 | Chen et al. .................. 257/706 |

FOREIGN PATENT DOCUMENTS

DE         198 10 736        9/1999

* cited by examiner

Primary Examiner—Kamand Cuneo
Assistant Examiner—I B Patel
(74) Attorney, Agent, or Firm—Young & Basile, PC

(57) ABSTRACT

A design for constructing an input circuit to receive and process an electrical signal, such as a voltage signal from a voltage source, where the input circuit has an extremely high resistance of at least $10^{11}$ ohms and is located on a printed circuit board. A first area of the printed circuit board carrying components of the input circuit is separated from a second area surrounding or contiguous to it by a channel-shaped recess to preserve the high resistance of the circuit even under operating conditions and at high relative humidity. The circuit is configured in such a way that the channel-shaped recess terminates in the interior of the printed circuit board and is extended in the direction of the thickness of the printed circuit board immediately up to a moisture-impermeable barrier layer which underlies the first area of the printed circuit board. The channel-shaped recess and the first area are filled and surrounded by a cohesive moisture-impermeable material.

8 Claims, 1 Drawing Sheet

DESIGN FOR CONSTRUCTING AN INPUT CIRCUIT TO RECEIVE AND PROCESS AN ELECTRICAL SIGNAL

BACKGROUND

The invention relates to a design for constructing an input circuit to receive and process an electrical signal, such as a voltage signal from a voltage source, specifically from a sensor, such as an electrochemical, inductive or optical sensor, where the input circuit has an extremely high input resistance of at least $10^{11}$ ohms and is located on a printed circuit board, where an first area of the printed circuit board carrying input circuit components is separated from a second area, which surrounds it or is contiguous to it, by a channel-shaped recess.

Specifically the present invention relates to an input circuit for measurement processing equipment to operate a sensor, specifically an electrochemical sensor for measuring pH. The sensor electrodes constitute a voltage source with an internal resistance of up to 1 gigohm. In order to be able to receive and process these voltages and thus measurement signals from the sensor, a suitable input circuit is required which puts such a small load on the voltage source that the error resulting from the reception and processing of the measurement signal is smaller than the acceptable measurement error. Normally an input resistance is required which is than the internal resistance of the electrode array of the sensor higher by a factor of 1000. The input resistance must be at least $10^{11}$ ohms, preferably $5 \times 10^{11}$ ohms. The preference is for $10^{13}$ ohms and higher.

An input circuit, particularly for recording the measurement signal from a pH-sensitive electrode array, normally comprises a high-resistance operational amplifier, which is wired in the circuit as a buffer (1 amplification) and thus amplifies the measurement signal for further processing of the measurement voltage. If an input circuit of this type is located on conventional printed circuit board material, specifically FR4 material, it operates reliably only under laboratory conditions, because under laboratory conditions (suitable temperature, low relative humidity) hardly any leakage current is drained off over the base material of the printed circuit board and of its surface and the surface of components involved.

However, if the input circuit is exposed to higher relative humidity and temperature under operating conditions (for example, 60°, 95 percent relative humidity), there is a risk that the reading will be falsified because of current leakage across the lower resistance base material on the circuit card, as a result of penetration of water molecules, as well as from current bridges, for example, across etched-in dirt particles on the surfaces of the input circuit and circuit card components. Without special measures, moisture cannot be prevented from penetrating into the base material of standard circuit cards. Standard circuit cards are constructed on a fiberglass-reinforced epoxy resin base and typically are capable of absorbing moisture. Water molecules can become embedded in the chemical structure of the epoxy resin. Furthermore water molecules can migrate by capillary action to the adjacent surfaces between the epoxy resin and embedded glass fibers into the interior of the printed circuit board.

This problem has been solved until now by the use of ceramic base material (so-called hybrid printed circuit boards) and an encapsulation of the input circuit by means of a high-fill, epoxy-based sealing material. This solution is relatively expensive, however, because of the costly material and is associated with time-intensive manufacturing.

In the applicant's patent DE 198 10 736 A1, a measurement input for a high-resistance input circuit was proposed, where a section of the printed circuit board assigned to the measurement input is isolated from the other areas of the printed circuit board by a dividing gap passing completely across the printed circuit board. This section is connected to an operational amplifier which, however, is not provided on the isolated section of the printed circuit board. It was possible to produce a high-resistance input circuit of this type under DE 198 10 736 A1 economically by assembling the printed circuit board in automated pick-and-place equipment and subsequently creating an insular section as the measurement input for the circuit. Taking this as a point of departure, the object of the present invention is to effectively counteract the effects of moisture on the input circuit.

In addition, as already mentioned above, the use of a ceramic base material (hybrid printed circuit board) as base material in place of conventional printed circuit board materials (FR4 material) and locating the components of the input circuit on it is already known. By encapsulating the input circuit with a high-fill, epoxy-based sealant it was possible to obtain the requisite input resistances on the input circuit. However, as already mentioned, this solution is expensive and time-intensive in production.

In contrast, the object is to bring about more economical manufacturability

SUMMARY

The preceding aspects of the object are met under the invention in a high-resistance input circuit of the generic type by having the channel-shaped recess in the interior of the printed circuit board stop, at least in sections not form a dividing gap passing completely through the printed circuit board, as in DE 198 10 736 A1, and extend directly in the direction of its thickness as far as a moisture-impermeable barrier layer (diffusion dam) which underlies the first area of the printed circuit board and by having the channel-shaped recess and the first area filled and enclosed by a cohesive moisture-impermeable sealing material.

The high-resistance components of the input circuit are therefore placed on the first area, which is made of conventional printed circuit board material, specifically FR-4 printed circuit board material, and overlaid by the moisture-impermeable sealing material. This first printed circuit board area is closed and sealed in a moisture-tight manner to the bottom and to the inside, specifically by the moisture-impermeable barrier layer on one side and laterally by the sealing material which fills the circumferential channel-shaped recess. As a result of the circumferential channel-shaped recess being extended right up to the moisture-impermeable barrier layer, complete sealing of the first printed circuit board area against moisture is achieved. So if any moisture which has found its way into the printed circuit board material penetrates from the inside in the direction of the first area on which the input circuit is located, the moisture is prevented from progressing to the circuit components by the moisture-impermeable barrier layer and by the sealing material filling the channel-shaped recess. The moisture-impermeable barrier coat can be achieved or configured in any way as long as effective blocking action against penetrating moisture is obtained. It has proved to be effective if the moisture-impermeable barrier layer is formed by a metallic layer inside the printed circuit board. This metallic layer is preferably flat, it extends continuously under the first area, that is without any breaks. The primary material of the printed circuit board can be a copper-clad printed circuit board, specifically a multi-layer printed circuit board. With respect to economical manufacturability of the printed circuit board, it proves to be advantageous if it is made from conventional FR-4 material, which has at least one moisture-impermeable barrier layer on the inside.

It has furthermore proved to be quite particularly advantageous if the walls of the printed circuit board adjacent to the channel-shaped recess have been furnished on their part with a moisture-impermeable coating, specifically in the form of a metal plating prior to pouring in the sealing material. This moisture-impervious coating is then in direct contact with the moisture-impervious barrier layer which underlies the first area of the printed circuit board and seals it against moisture. The moisture-impervious sealing material is produced on an epoxy base or on a high-density polyethylene or liquid resin base.

BRIEF DESCRIPTION OF THE DRAWING

Additional features, details and advantages of the invention can be seen from the attached patent claims and from the graphic representation and the subsequent description of a preferred embodiment of the invention. In the drawing:

DETAILED DESCRIPTION

Figure 1:
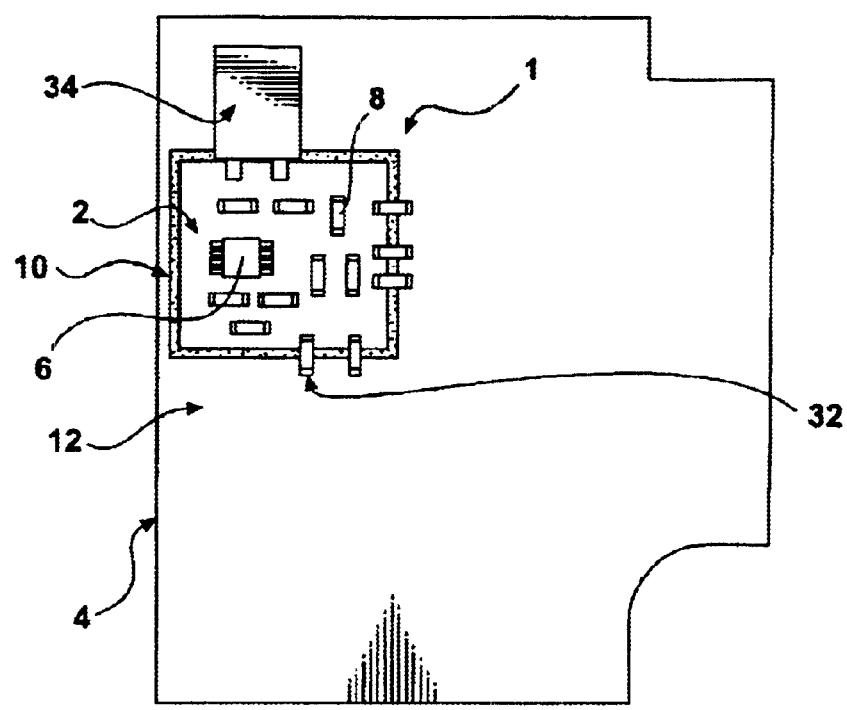
FIG. 1 shows a schematic plan view of a printed circuit board having an input circuit under the invention (shown schematically) for the measurement signal from a sensor.

FIG. 1 shows a plan view onto a printed circuit board having a high resistance input circuit 1 for the measurement signal from a glass-based pH-sensor, where one sensor electrode is formed by a glass encapsulation of a measurement cell electrolyte.

The input circuit 1 is located on a first printed circuit board area 2 of a printed circuit board 4, identified in its entirety with the reference numeral 4 and made of a conventional FR4 material. The printed circuit board 4 contains electrical and electronic components, such as an operational amplifier 6, resistances 8 and capacitors. The first printed circuit board area 2, which forms a high-resistance section of the printed circuit board 4, is separated in the plan view of FIG. 1 from the remaining second area 12 of the printed circuit board 4 by a circumferential channel-shaped recess 10.

Figure 2:
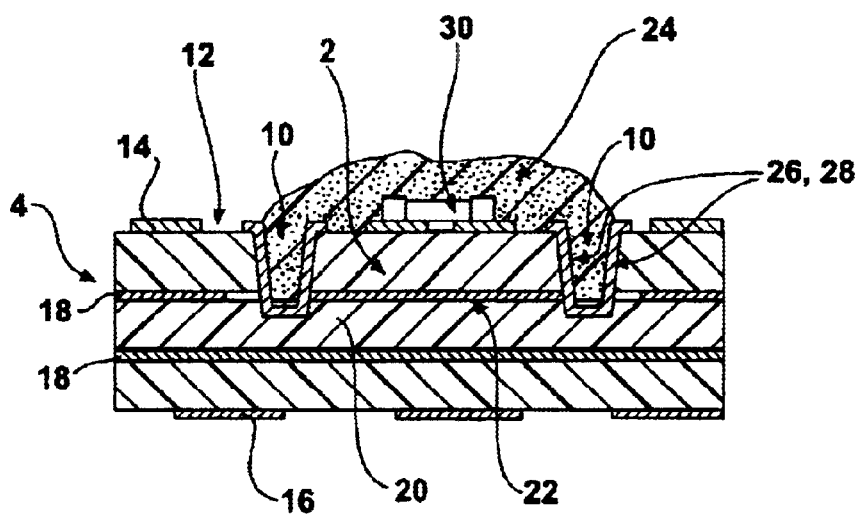
FIG. 2 shows a sectional view of a printed circuit board with a schematic representation of an input circuit.

FIG. 2 shows a schematic sectional view of the structure of the printed circuit board 4 with the input circuit, where the illustration cannot be assigned to any particular sectional plane in FIG. 1, but is only a schematic representation of the structure, where corresponding parts are given the same reference numeral. FIG. 2 shows the printed circuit board 4 formed from three layers of FR4 material, which is copper-clad on both sides, where partial breaks have been introduced in the outer copper layers 14, 16 during production. The printed circuit board 4 comprises in its interior additional metal layers 18, 19. The first printed circuit board area 2 previously mentioned in connection with FIG. 1 is bordered by the circumferential channel-shaped recess 10 and thereby separated from the other second printed circuit board area 12 in the plan view in FIG. 1. As can be seen from FIG. 2, the channel-shaped recess 10 terminates in the interior of the printed circuit board 4 so that no continuous island is formed as under DE 198 01 736 A mentioned above. The possibility would not be excluded that the sections of the channel-shaped recess 10 could extend through to the other side. However, it is essential that the layer 18, which underlies the first area 2 of the printed circuit board 4, is reached when introducing the channel-shaped recess, for example, by routing. This area of the layer 18 forms a fluid and moisture-impermneable barrier layer, so that a moisture-impermeable encapsulation of the first area 2 and of the input circuit located on it is achieved. At least that section 22 of the layer 18 which underlies the first area 2 is moisture-impermeable and forms the barrier layer 20; preferably this is the metallic layer 18. Then either a moisture-impermeable sealing material 24, which is also poured into the channel-shaped recess 10, can be immediately adjacent to this section 22 or the barrier layer 20 respectively and thus form a moisture-impermeable encapsulation, or—as in the situation depicted in FIG. 2—walls 26 on the printed circuit board, which border the channel-shaped recess 10, are furnished with a moisture-impermeable layer of this type, preferably a metal coating 28 which for its part is contiguous with the barrier layer 20 and is attached continuously to it in a fluid-tight manner along its edges. In this way, a moisture-impermeable, preferably metallic, sink is formed which borders the first area 2 on which the input circuit is located. Furthermore, after assembling the components on the printed circuit board 4 (only one component 30 of the input circuit is shown schematically) a moisture-impermeable, epoxy-based sealing material 24 is poured both into the depression formed by the channel-shaped recess 10 as well as over the entire first area 2. It was determined that encapsulation of this type of the input circuit does not allow moisture to reach the input circuit, either from outside or from inside. It is possible to work with conventional printed circuit board materials which can absorb and conduct moisture within the printed circuit board. By providing the moisture-impermeable barrier layer 20 in the form of section 22 of the layer 18, the second area 2 of the printed circuit board 4 carrying the input circuit can be insulated effectively to the inside. No moisture enters the second area 2 and thus does not reach the high-resistance circuit section. To the outside, the sealing material 24 forms a moisture-proof termination. In this way the high-resistance condition existing at the time of production remains intact even under operating conditions.

Incoming or outgoing signals to or from the input circuit are received or transmitted respectively through resistances 32, the pad of one of which is located in the interior of the encapsulated area and the pad of the other of which is located in the outer second area 12 of the printed circuit board. The sealing material surrounds the normally ceramic body of the resistance 32 in such a way that no moisture can penetrate. The contacts for the measurement signal from the pH-sensor can be provided through a Teflon connector 34. Because of the poor adhesion of Teflon to the sealing materials under discussion here, the Teflon housing body of the connector 34 is positioned outside the sealing material 24, where the pads of the connector, however, extend through the sealing material 24.

Attention must be drawn to the fact that the surface area of the printed circuit board, namely the first area 2, on which the input circuit components are to be installed, is not provided with an additional coating, for example, solder resist, in order not to jeopardize the high resistance between the conductor paths.

What is claimed is:

1. A design for constructing an input circuit to receive and process an electrical signal, such as a voltage signal from a voltage source, specifically from a sensor where the input circuit has an extremely high input resistance of at least $10^{11}$ ohms and is located on a printed circuit board, where a first area carrying input circuit components of the printed circuit board is separated by a channel-shaped recess from a surrounding second area, characterized in that the channel-shaped recess terminates in the interior of the printed circuit board and is extended in the direction of the thickness of the printed circuit board beyond a moisture-impervious barrier layer-which underlies the first area of the printed circuit board, and in that the channel-shaped recess and the first area are filled and enclosed by a cohesive moisture-impermeable sealing material.

2. The design in accordance with claim 1, wherein the moisture-impermeable barrier layer is a metallic layer.

3. The design in accordance with claim 2, wherein the metallic layer forms a flat layer inside the printed circuit board and is configured uninterruptedly at least under the first area.

4. The design in accordance with claim 1, wherein the printed circuit board is made from an FR4 material, which has at least one moisture-impermeable barrier layer in its interior.

5. A design for constructing an input circuit to receive and process an electrical signal, wherein the input circuit has an extremely high input resistance of at least $10^{11}$ ohms and is located on a printed circuit board, where a first area carrying input circuit components of the printed circuit board is separated by a channel-shaped recess from a surrounding second area, characterized in that the channel-shaped recess terminates in the interior of the printed circuit board and is extended in the direction of the thickness of the printed circuit board at least as far as a moisture-impervious barrier layer which underlies the first area of the printed circuit board, and in that the channel-shaped recess and the first area are filled and enclosed by a moisture-impermeable sealing material, and in that walls of the printed circuit board bordering the channel-shaped recess are provided with a moisture-impermeable coating.

6. A design wherein for constructing an input circuit to receive and process an electrical signal, wherein the input circuit has an extremely high input resistance of at least $10^{11}$ ohms and is located on a printed circuit board, where a first area carrying input circuit components of the printed circuit board is separated by a channel-shaped recess from a surrounding second area, characterized in that the channel-shaped recess terminates in the interior of the printed circuit board and is extended in the direction of the thickness of the printed circuit board at least as far as a moisture-impervious barrier layer which underlies the first area of the printed circuit board, and in that the channel-shaped recess and the first area are filled and enclosed by a moisture-impermeable sealing material, and in that walls of the printed circuit board bordering the channel-shaped recess are provided with a moisture-impermeable coating, and in that the coating is formed from a metal alloy, which is attached in a fluid-tight manner to the barrier layer.

7. The design in accordance with one of the preceding claims, wherein the-moisture-impermeable sealing material is manufactured on a epoxy base or on a high-density polyethylene base or on a liquid resin base.

8. A circuit card for measurement processing equipment characterized by a design in accordance with claim 1.

* * * * *